(12) United States Patent
Ozinga et al.

(10) Patent No.: US 8,945,166 B2
(45) Date of Patent: Feb. 3, 2015

(54) APPARATUS AND METHOD FOR FORMING INCISIONS IN OCULAR TISSUE

(71) Applicant: Refocus Group, Inc., Dallas, TX (US)

(72) Inventors: David G. Ozinga, Double Oak, TX (US); Karl H. Beitzel, Canton, OH (US)

(73) Assignee: Refocus Group, Inc., Dallas, TX (US)

( * ) Notice: Subject to any disclaimer, the term of this patent is extended or adjusted under 35 U.S.C. 154(b) by 0 days.

(21) Appl. No.: 14/070,135

(22) Filed: Nov. 1, 2013

(65) Prior Publication Data

US 2014/0074137 A1    Mar. 13, 2014

Related U.S. Application Data

(62) Division of application No. 13/205,359, filed on Aug. 8, 2011, now Pat. No. 8,597,318.

(51) Int. Cl.
```
A61B 17/14      (2006.01)
A61B 17/32      (2006.01)
A61F 9/013      (2006.01)
A61B 17/3209    (2006.01)
A61F 9/007      (2006.01)
```

(52) U.S. Cl.
CPC .......... *A61F 9/0133* (2013.01); *A61B 17/3209* (2013.01); *A61F 9/00736* (2013.01); *A61B 17/32002* (2013.01)
USPC ...................................................... 606/180

(58) Field of Classification Search
USPC ......... 606/166, 167, 168, 170, 171, 177, 178, 606/180; 30/261, 296, 43.4, 43.5, 477, 903, 30/388, 240, 276, 347
See application file for complete search history.

(56) References Cited

U.S. PATENT DOCUMENTS

| | | | |
|---|---|---|---|
| 1,905,851 | A | 4/1933 | Green |
| 2,104,929 | A | 1/1938 | Kendall |
| 2,249,906 | A | 7/1941 | Longoria |
| 2,580,138 | A | 12/1951 | Trought |
| 2,942,483 | A | 6/1960 | Thomas |
| 3,609,864 | A | 10/1971 | Bassett |
| 3,814,213 | A | 6/1974 | Balass |
| 3,922,784 | A | 12/1975 | Prince et al. |

(Continued)

FOREIGN PATENT DOCUMENTS

| | | |
|---|---|---|
| DE | 2226908 | 12/1972 |
| EP | 0 083 494 A1 | 7/1983 |

(Continued)

OTHER PUBLICATIONS

Office Action dated May 13, 2009 in connection with U.S. Appl. No, 11/698,008.

(Continued)

*Primary Examiner* — Katherine M Shi

(57) ABSTRACT

A surgical tool includes a rocker assembly configured to cause rotation of a surgical blade to form an incision. The rocker assembly includes a gear. The surgical tool also includes a ratchet configured to rotate in a first direction and a second direction. The surgical tool further includes a linkage arm connecting the rocker assembly and the ratchet so that rotation of the ratchet causes rotation of the rocker assembly. In addition, the surgical tool includes a spring configured to be extended by the ratchet when the ratchet is rotated in the first direction. The spring is also configured to retract and cause the ratchet to rotate in the second direction.

20 Claims, 12 Drawing Sheets

(56) References Cited

U.S. PATENT DOCUMENTS

| | | |
|---|---|---|
| 4,052,988 A | 10/1977 | Doddi et al. |
| 4,071,029 A | 1/1978 | Richmond et al. |
| 4,340,059 A | 7/1982 | Marinoff |
| 4,349,027 A | 9/1982 | DiFrancesco |
| 4,452,235 A | 6/1984 | Reynolds |
| 4,601,290 A | 7/1986 | Effron et al. |
| 4,649,919 A | 3/1987 | Thimsen et al. |
| 4,669,466 A | 6/1987 | L'Esperance |
| 4,672,964 A | 6/1987 | Dee et al. |
| 4,688,570 A | 8/1987 | Kramer et al. |
| 4,753,655 A | 6/1988 | Hecht |
| 4,819,631 A | 4/1989 | Poley |
| 4,955,882 A | 9/1990 | Hakky |
| 4,986,807 A | 1/1991 | Farr |
| 5,002,564 A | 3/1991 | McGregor et al. |
| 5,006,123 A | 4/1991 | Soll et al. |
| 5,090,955 A | 2/1992 | Simon |
| 5,098,438 A | 3/1992 | Siepser |
| 5,098,443 A | 3/1992 | Parel et al. |
| 5,188,125 A | 2/1993 | Kilmer et al. |
| 5,201,704 A | 4/1993 | Ray |
| 5,203,865 A | 4/1993 | Siepser |
| 5,215,104 A | 6/1993 | Steinert |
| 5,222,959 A | 6/1993 | Anis |
| 5,224,950 A | 7/1993 | Prywes |
| 5,314,441 A | 5/1994 | Cusack et al. |
| 5,342,377 A | 8/1994 | Lazerson |
| 5,423,841 A | 6/1995 | Kornefeld |
| 5,431,671 A | 7/1995 | Nallakrishnan |
| 5,441,510 A | 8/1995 | Simpson et al. |
| 5,492,528 A | 2/1996 | Anis |
| 5,522,829 A | 6/1996 | Michalos |
| 5,547,468 A | 8/1996 | Simon et al. |
| 5,571,106 A | 11/1996 | Coufal et al. |
| 5,618,294 A | 4/1997 | Aust et al. |
| 5,624,456 A | 4/1997 | Hellenkamp |
| 5,651,782 A | 7/1997 | Simon et al. |
| 5,695,511 A | 12/1997 | Cano et al. |
| 5,779,723 A | 7/1998 | Schwind |
| 5,817,115 A | 10/1998 | Nigam |
| 5,908,433 A | 6/1999 | Eager et al. |
| 6,007,578 A | 12/1999 | Schachar |
| 6,033,437 A | 3/2000 | Perry |
| 6,050,999 A | 4/2000 | Paraschac et al. |
| 6,051,009 A | 4/2000 | Hellenkamp et al. |
| 6,051,023 A | 4/2000 | Kilmer et al. |
| 6,077,287 A | 6/2000 | Taylor et al. |
| 6,080,172 A | 6/2000 | Fujiware et al. |
| 6,117,149 A | 9/2000 | Sorensen et al. |
| 6,171,336 B1 | 1/2001 | Sawusch |
| 6,231,583 B1 | 5/2001 | Lee |
| 6,264,668 B1 | 7/2001 | Prywes |
| 6,328,747 B1 | 12/2001 | Nun |
| 6,358,262 B1 | 3/2002 | Chan et al. |
| 6,409,740 B1 | 6/2002 | Kuhr et al. |
| 6,443,966 B1 | 9/2002 | Shiu |
| 6,565,584 B1 | 5/2003 | Mathis et al. |
| 6,602,266 B1 | 8/2003 | Loomas et al. |
| 6,605,093 B1 | 8/2003 | Blake |
| 6,610,075 B1 | 8/2003 | Levesque et al. |
| 6,692,524 B2 | 2/2004 | Baikoff |
| 6,926,727 B2 | 8/2005 | Schachar et al. |
| 7,189,248 B2 | 3/2007 | Schachar et al. |
| 7,763,042 B2 | 7/2010 | Iio et al. |
| 7,901,421 B2 | 3/2011 | Shiuey et al. |
| 2002/0077642 A1 | 6/2002 | Patel et al. |
| 2002/0116062 A1 | 8/2002 | Portney |
| 2002/0120284 A1 | 8/2002 | Schachar et al. |
| 2002/0120285 A1 | 8/2002 | Schachar et al. |
| 2003/0097080 A1 | 5/2003 | Esashi et al. |
| 2003/0120295 A1 | 6/2003 | Simpson et al. |
| 2004/0073303 A1 | 4/2004 | Schanzlin et al. |
| 2005/0131441 A1 | 6/2005 | Iio et al. |
| 2006/0106408 A1 | 5/2006 | Schachar et al. |
| 2006/0106409 A1 | 5/2006 | Schachar et al. |
| 2006/0259060 A1 | 11/2006 | Whitson et al. |
| 2007/0078471 A1 | 4/2007 | Schachar et al. |
| 2007/0123919 A1 | 5/2007 | Schachar et al. |
| 2008/0234693 A1 | 9/2008 | Stefanchik |
| 2009/0157109 A1 | 6/2009 | Bare et al. |

FOREIGN PATENT DOCUMENTS

| | | |
|---|---|---|
| EP | 1 764 037 A1 | 3/2007 |
| JP | 61170449 | 8/1986 |
| JP | 2003530975 A | 10/2003 |
| JP | 2004503276 A | 2/2004 |
| JP | 20052379645 A | 9/2005 |
| WO | WO 94/03129 A1 | 2/1994 |
| WO | WO 94/18636 A2 | 8/1994 |
| WO | WO 98/42409 A1 | 10/1998 |
| WO | WO 99/17684 A1 | 4/1999 |
| WO | WO 99/17691 A1 | 4/1999 |
| WO | WO 99/30645 A2 | 6/1999 |
| WO | WO 99/30656 A1 | 6/1999 |
| WO | WO 00/74600 A1 | 12/2000 |
| WO | WO 01/45607 A1 | 6/2001 |
| WO | WO 01/95783 A2 | 12/2001 |
| WO | WO 2005/084557 A1 | 9/2005 |

OTHER PUBLICATIONS

Office Action dated Apr. 8, 2009 in connection with U.S. Appl. No. 11/606,480.

Office Action dated Nov. 2, 2009 in connection with U.S. Appl. No. 11/606,480.

Office Action dated Nov. 25, 2009 in connection with U.S. Appl. No. 11/199,591.

Michael R. Bryant et al., "Computer-Aided Surgical Design in Refractive Keratotomy", The CLAO Journal, vol. 13, No. 4, Jul. 1987, pp. 238-242.

Notification of Transmittal of the International Search Report or the Declaration dated Mar. 6, 2008 in PCT Application No. PCT/US03/15896.

Spencer P. Thornton, "Anterior Ciliary Sclerotomy (ACS), A Procedure to Reverse Presbyopia", Surgery for Hyperopia and Presbyopia, 1997, pp. 33-36.

Office Action dated Jun. 10, 2010 in connection with U.S. Appl. No. 11/199,591.

Office Action dated Jun. 21, 2011 in connection with U.S. Appl. No. 11/199,591.

Translation of Office Action issued on Feb. 8, 2008 in Japanese Patent Application No. 2002-567203.

The Surgical Armamentarium (American v. Mueller), 1980, p. 4, Figure C.

Office Action dated Nov. 18, 2011 in connection with U.S. Appl. No. 11/199,591.

Office Action dated Nov. 17, 2009 in connection with U.S. Appl. No. 10/443,122.

Office Action dated Dec. 9, 2009 in connection with U.S. Appl. No. 11/698,008.

Office Action dated Jul. 1, 2009 in connection with U.S. Appl. No. 11/323,284.

Office Action dated Sep. 22, 2009 in connection with U.S. Appl. No. 11/323,283.

Office Action dated May 14, 2013 in connection with U.S. Appl. No. 11/606,480.

Translation of Office Action dated Dec. 4, 2012 in connection with Japanese Patent Application No. 2010-532244.

Office Action dated Dec. 6, 2012 in connection with U.S. Appl. No. 11/606,480.

European Search Report dated Sep. 3, 2012 in connection with European Patent Application No. EP 12 17 7148.

Notification of Transmittal of the International Search Report and the Written Opnion of the International Searching Autority, or the Declaration dated Oct. 22, 2012 in connection with International Patent Application No. PCT/US12/49986.

Notification of Transmittal of the International Search Report and the Written Opinion of the International Searching Authority, or the Declaration dated Apr. 14, 2009 in connection with PCT Application No. PCT/US2008/081808.

APPARATUS AND METHOD FOR FORMING INCISIONS IN OCULAR TISSUE

CROSS-REFERENCE TO RELATED PATENT DOCUMENTS

This application is a division of prior U.S. patent application Ser. No. 13/205,359 filed on Aug. 8, 2011, which is related to the following U.S. patent applications and issued patents:
 (1) U.S. Pat. No. 6,007,578 entitled "Scleral Prosthesis for Treatment of Presbyopia and Other Eye Disorders";
 (2) U.S. Pat. No. 6,280,468 entitled "Scleral Prosthesis for Treatment of Presbyopia and Other Eye Disorders";
 (3) U.S. Pat. No. 6,299,640 entitled "Scleral Prosthesis for Treatment of Presbyopia and Other Eye Disorders";
 (4) U.S. Pat. No. 6,991,650 entitled "Scleral Expansion Device Having Duck Bill";
 (5) U.S. Pat. No. 7,008,396 entitled "Ophthalmic Device and Method of Manufacture and Use";
 (6) U.S. Pat. No. 7,416,560 entitled "Scleral Prosthesis for Treatment of Presbyopia and Other Eye Disorders";
 (7) U.S. Pat. No. 7,780,727 entitled "Scleral Prosthesis for Treatment of Presbyopia and Other Eye Disorders";
 (8) U.S. Pat. No. 7,785,367 entitled "Scleral Prosthesis for Treatment of Presbyopia and Other Eye Disorders";
 (9) U.S. Pat. No. 7,927,372 entitled "Scleral Prosthesis Having Crossbars for Treating Presbyopia and Other Eye Disorders";
 (10) U.S. patent application Ser. No. 11/827,382 entitled "Scleral Prosthesis for Treating Presbyopia and Other Eye Disorders and Related Devices and Methods";
 (11) U.S. patent application Ser. No. 12/960,917 entitled "Scleral Prosthesis for Treating Presbyopia and Other Eye Disorders and Related Devices and Methods";
 (12) U.S. Pat. No. 6,926,727 entitled "Surgical Blade for Use with a Surgical Tool for Making Incisions for Scleral Eye Implants";
 (13) U.S. Pat. No. 7,189,248 entitled "System and Method for Making Incisions for Scleral Eye Implants";
 (14) U.S. Pat. No. 7,824,423 entitled "System and Method for Making Incisions for Scleral Eye Implants";
 (15) U.S. Pat. No. 7,854,742 entitled "System and Method for Making Incisions for Scleral Eye Implants";
 (16) U.S. patent application Ser. No. 12/260,694 entitled "Apparatuses and Methods for Forming Incisions in Ocular Tissue";
 (17) U.S. patent application Ser. No. 11/827,444 entitled "Apparatus and Method for Securing Ocular Tissue";
 (18) U.S. Pat. No. 7,909,780 entitled "System and Method for Determining a Position for a Scleral Pocket for a Scleral Prosthesis"; and
 (19) U.S. patent application Ser. No. 12/416,868 entitled "System and Method for Identifying a Position to Insert a Scleral Prosthesis into an Eye".
All of these U.S. patents and patent applications are hereby incorporated by reference.

TECHNICAL FIELD

This disclosure is generally directed to surgical devices. More specifically, this disclosure relates to an apparatus and method for forming incisions in ocular tissue.

BACKGROUND

Various surgical procedures may be performed on a patient's eye to reduce or correct any number of vision problems. For example, surgical procedures are often performed to treat presbyopia, myopia, hyperopia, elevated intraocular pressure, ocular hypertension, and glaucoma.

As a particular example, presbyopia can often be treated by implanting scleral prostheses within the scleral tissue of the patient's eye as described in various patent documents incorporated by reference above. For each scleral prosthesis, an incision can be made in the sclera and extended under the surface of the sclera to form a scleral tunnel, and the scleral prosthesis can be placed within the tunnel. One or multiple scleral prostheses may be implanted in a patient's eye to partially or completely eliminate presbyopia in the patient's eye. The same or similar technique can also be used to treat glaucoma, ocular hypertension, elevated intraocular pressure, or other eye disorders.

SUMMARY

This disclosure provides an apparatus and method for forming incisions in ocular tissue.

In a first embodiment, a surgical tool includes a rocker assembly configured to cause rotation of a surgical blade to form an incision. The rocker assembly includes a gear. The surgical tool also includes a ratchet configured to rotate in a first direction and a second direction. The surgical tool further includes a linkage arm connecting the rocker assembly and the ratchet so that rotation of the ratchet causes rotation of the rocker assembly. In addition, the surgical tool includes a spring configured to be extended by the ratchet when the ratchet is rotated in the first direction. The spring is also configured to retract and cause the ratchet to rotate in the second direction.

In a second embodiment, a surgical tool includes a drive belt configured to rotate a surgical blade to form an incision. The surgical tool also includes a spring-loaded ratchet configure to rotate in a first direction to extend a spring and to rotate in a second direction when the spring retracts. In addition, the surgical tool includes a gear configured to rotate in response to rotation of the ratchet, where the gear is configured to rotate the drive belt in order to rotate the surgical blade.

In a third embodiment, a method includes rotating a ratchet in a first direction to extend a spring in a surgical tool and rotating a surgical blade forward and backward a first time based on the rotation of the ratchet in the first direction. The method also includes locking the ratchet after the rotation in the first direction to place the surgical tool in a loaded state. The method further includes firing the loaded surgical tool by releasing the ratchet so that the ratchet rotates in a second direction as the spring pulls the ratchet. In addition, the method includes rotating the surgical blade forward and backward a second time based on the rotation of the ratchet in the second direction.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawing, in which.

DETAILED DESCRIPTION

FIGS. 1 through 6, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
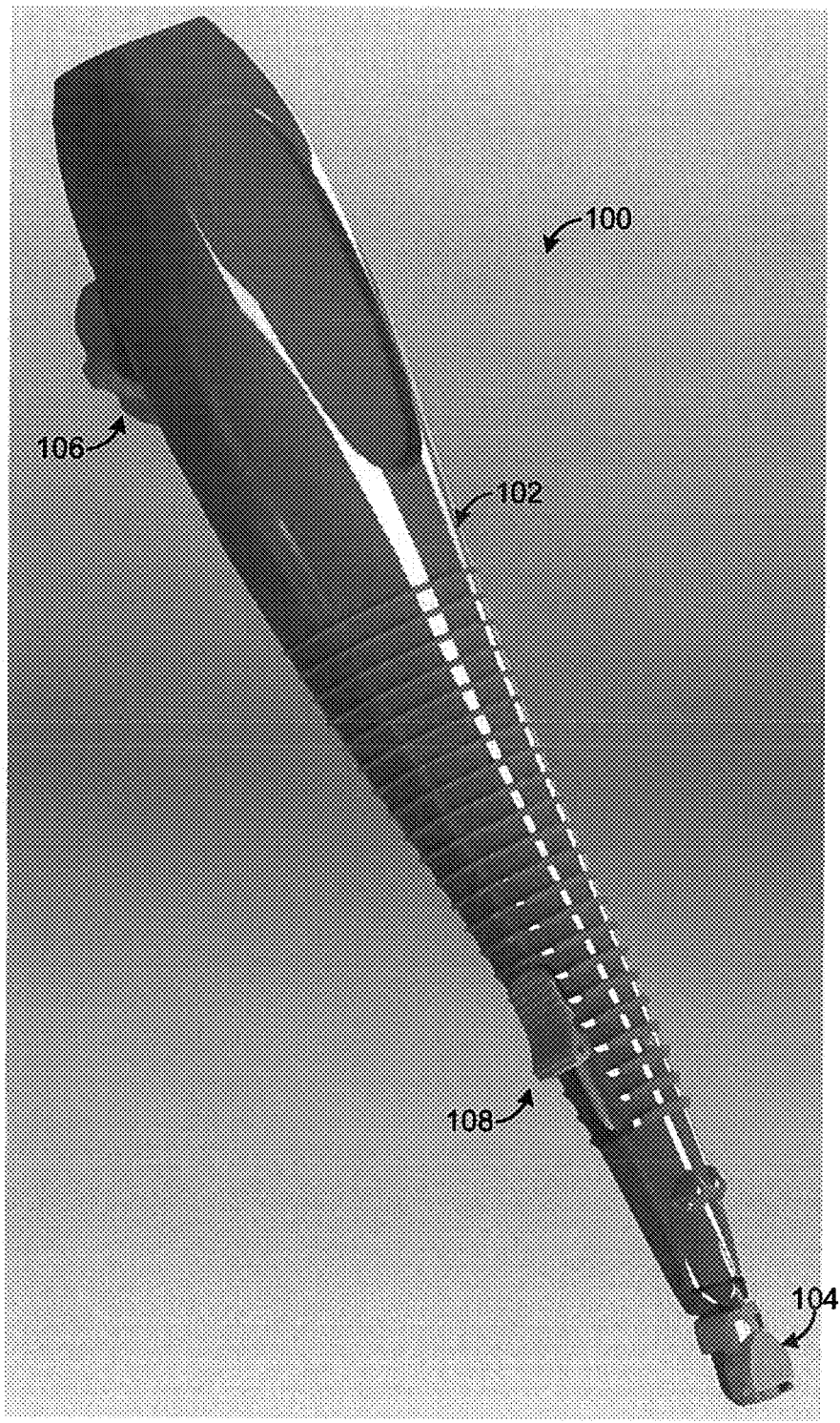
FIG. 1 illustrates an example surgical tool for making incisions in ocular tissue in accordance with this disclosure.
Figure 2:
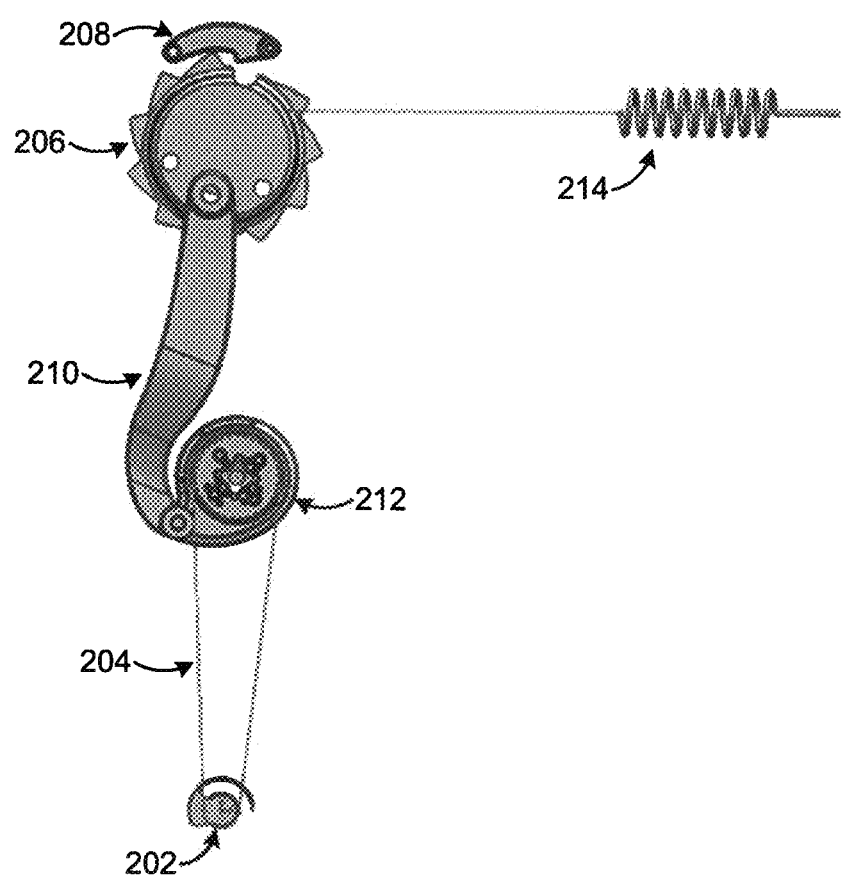
FIG. 2 illustrates example components within the surgical tool of FIG. 1 in accordance with this disclosure.

FIG. 1 illustrates an example surgical tool 100 for making incisions in ocular tissue in accordance with this disclosure. As shown in FIG. 1, the surgical tool 100 includes a housing 102 and a surgical blade assembly 104. The housing 102 contains various components that cause rotation of a surgical blade in the surgical blade assembly 104. Example components within the housing 102 are shown in FIG. 2, which is described below. The housing 102 includes any suitable structure containing and supporting other components of the surgical tool 100. The housing 102 could have any suitable size and shape and be formed from any suitable material(s), such as plastic.

The surgical blade assembly 104 includes a surgical blade that is rotated to physically form an incision in the ocular tissue of a patient's eye. The surgical blade assembly 104 can also include other structures facilitating rotation of the surgical blade, such as a drive gear or other structure that can be rotated by other components within the housing 102. The surgical blade assembly 104 includes any suitable structure having a blade that forms an incision in ocular tissue.

Although not shown, the surgical tool 100 could include a footplate attached to the bottom of the surgical tool 100. The footplate represents a structure that can be placed onto the surface of a patient's eye. The footplate allows the surgical tool 100 to be placed on the patient's eye to ensure that any incisions made by the surgical tool 100 are in the proper positions on and at the proper depths in the patient's eye. In some embodiments, the footplate includes two notches, which allow the tip of the surgical blade to pass through the footplate and into and out of the patient's ocular tissue. The footplate includes any suitable structure facilitating placement of the surgical tool 100 on a patient's eye.

As described in more detail below, the surgical tool 100 includes a spring-loaded mechanism, which uses a spring to create rotation of the surgical blade in the surgical blade assembly 104. When triggered, the spring rotates a ratchet to cause the surgical blade to rotate into and then out of the patient's eye, creating an incision. At that point, the incision can be used in any suitable manner, such as by inserting a scleral prosthesis into the incision as described in various patent documents incorporated by reference above.

To support this functionality, the surgical tool 100 can include various controls. For example, an external knob 106 can be turned by an operator to "load" the spring-loaded mechanism, preparing the surgical tool 100 for use. Also, a trigger 108 can be used to "fire" the spring-loaded mechanism, causing the surgical blade to rotate and form an incision. Note, however, that other types of controls could be used. For example, one or more actuators could be used to load and/or fire the spring-loaded mechanism. These actuators could be controlled in any suitable manner, such as via infrared or other signals (wired or wireless) from a surgeon's footplate or other control device.

FIG. 2 illustrates example components within the surgical tool 100 of FIG. 1 in accordance with this disclosure. These components could, for example, reside within the housing 102 and operate to rotate a surgical blade 202. The surgical blade 202 forms part of the surgical blade assembly 104 of FIG. 1.

In this example, the surgical blade 202 includes a central portion and a curved cutting blade connected to the central portion. The central portion of the surgical blade 202 can be attached to and rotated by the surgical tool 100. Rotation of the central portion of the surgical blade 202 therefore results in movement of the cutting blade. By rotating the central portion of the surgical blade 202 in one direction, the cutting blade can be moved into ocular tissue of a patient's eye. By rotating the central portion of the surgical blade 202 in the opposite direction, the cutting blade can be retracted from the ocular tissue of the patient's eye. Here, the surgical blade 202 includes a curved cutting blade that can be used (among other things) to form scleral tunnels in the scleral tissue of the patient's eye. However, the surgical blade 202 could be used to form any other suitable incision, and the surgical blade 202 could use any suitable type of cutting blade (curved or otherwise). Also, in some embodiments, the surgical blade 202 could be replaceable so that the surgical tool 100 can be reused for multiple patients. In other embodiments, the surgical tool 100 could be disposable, and the surgical blade 202 may or may not be removable.

The central portion of the surgical blade 202 includes or is connected to a drive gear or other mechanism that operates in conjunction with a drive belt 204. The drive belt 204 represents a belt or other structure that can be rotated by other components of the surgical tool 100 to cause rotation of the surgical blade 202. As described in more detail below, the surgical tool 100 is configured to cause bi-directional rotation of the drive belt 204, thereby causing bi-directional rotation of the surgical blade 202 (into and then out of the patient's ocular tissue). The drive belt 204 includes any suitable structure facilitating rotation of the surgical blade 202, such as a belt or wire formed form rubber, plastic, metal, or other material(s).

The surgical tool 100 also includes a ratchet 206 and a pawl 208. The ratchet 206 represents a structure having teeth or other locking mechanisms that can be engaged by the pawl 208. As described in more detail below, the ratchet 206 can be rotated in one direction to load the surgical tool 100, and the pawl 208 can prevent rotation of the ratchet 206 in the other direction until the surgical tool 100 is fired. A cable or other connection could link the trigger 108 with the pawl 208 so that the pawl 208 rotates and allows the ratchet 206 to turn when the trigger 108 is activated. In this example, the pawl 208 can rotate around a pivot point at its right end, where the pawl 208 is connected to another structure (such as the housing 102). The left end of the pawl 208 can move down and up to engage and disengage the ratchet 206. The ratchet 206 includes any suitable structure having a locking mechanism to prevent rotation in one direction. The pawl 208 includes any suitable structure for preventing rotation of the ratchet 206 in one direction.

A linkage arm 210 connects the ratchet 206 with a rocker assembly 212. The upper end of the linkage arm 210 is rotatably connected to the ratchet 206, so the linkage arm 210 remains in a generally vertical position (as seen in FIG. 2) even as the ratchet 206 moves the upper end of the linkage arm 210 around a central axis of the ratchet 206. Rotation of the ratchet 206 causes the linkage arm 210 to generally move up and down, which causes the rocker assembly 212 to rotate the drive belt 204. The linkage arm 210 includes any suitable structure connecting the ratchet 206 and the rocker assembly 212.

The rocker assembly 212 includes a gear or other structure that engages the drive belt 204. For example, the drive belt 204 could loop around a portion of the gear in the rocker assembly 212, or the drive belt 204 could be wrapped around the gear in the rocker assembly 212 one or more times. When the linkage arm 210 moves upward in FIG. 2, the gear in the rocker assembly 212 rotates clockwise, causing the drive belt 204 to rotate the surgical blade 202 clockwise. When the linkage arm 210 moves downward in FIG. 2, the gear in the rocker assembly 212 rotates counterclockwise, causing the drive belt 204 to rotate the surgical blade 202 counterclockwise. This imparts bidirectional rotation to the surgical blade 202, allowing the surgical blade 202 to form an incision. The rocker assembly 212 includes any suitable structure for causing bidirectional rotation of the drive belt 204. An example embodiment of the rocker assembly 212 is shown in FIGS. 3A and 3B, which are described below.

At least one spring 214 is used to cause rotation of the ratchet 206. In the example shown in FIG. 2, the right end of the spring 214 can be connected to an external structure, such as the housing 102. Also, the left end of the spring 214 is connected to the ratchet 206 and can wrap around the ratchet 206. Alternatively, the spring 214 could be connected to a coupler that is wrapped around the ratchet 206. When the ratchet 206 is rotated counterclockwise in this example, this extends the spring 214, and the pawl 208 prevents the ratchet 206 from rotating clockwise. At this point, the surgical tool 100 is in a loaded condition. When the pawl 208 is released, the spring 214 pulls the ratchet 206 clockwise, firing the surgical tool 100. This imparts bidirectional rotation to the surgical blade 202. The spring 214 can be formed from any suitable material(s) and have any number of turns. Moreover, one or multiple springs 214 can be used to pull the ratchet 206 in one direction.

Figure 3A:
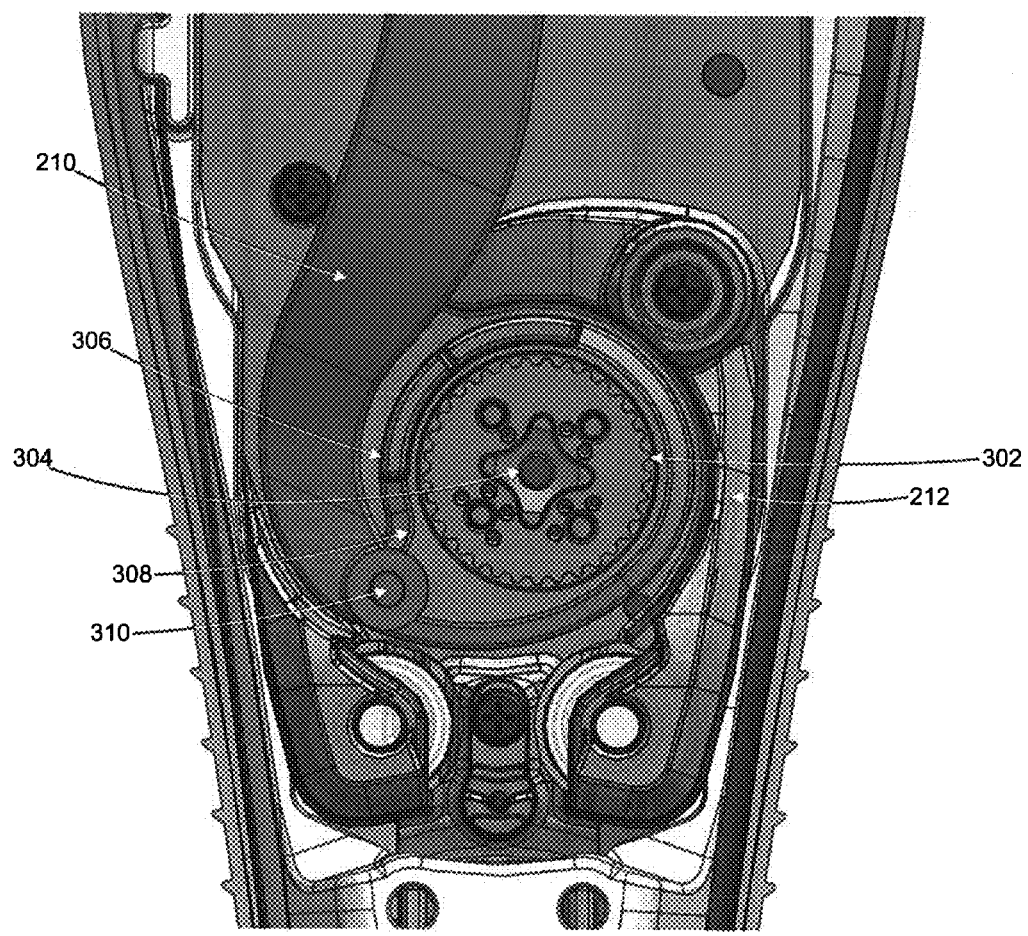
FIGS. 3A and 3B illustrate an example rocker assembly within the surgical tool of FIG. 1 in accordance with this disclosure.
Figure 3B:
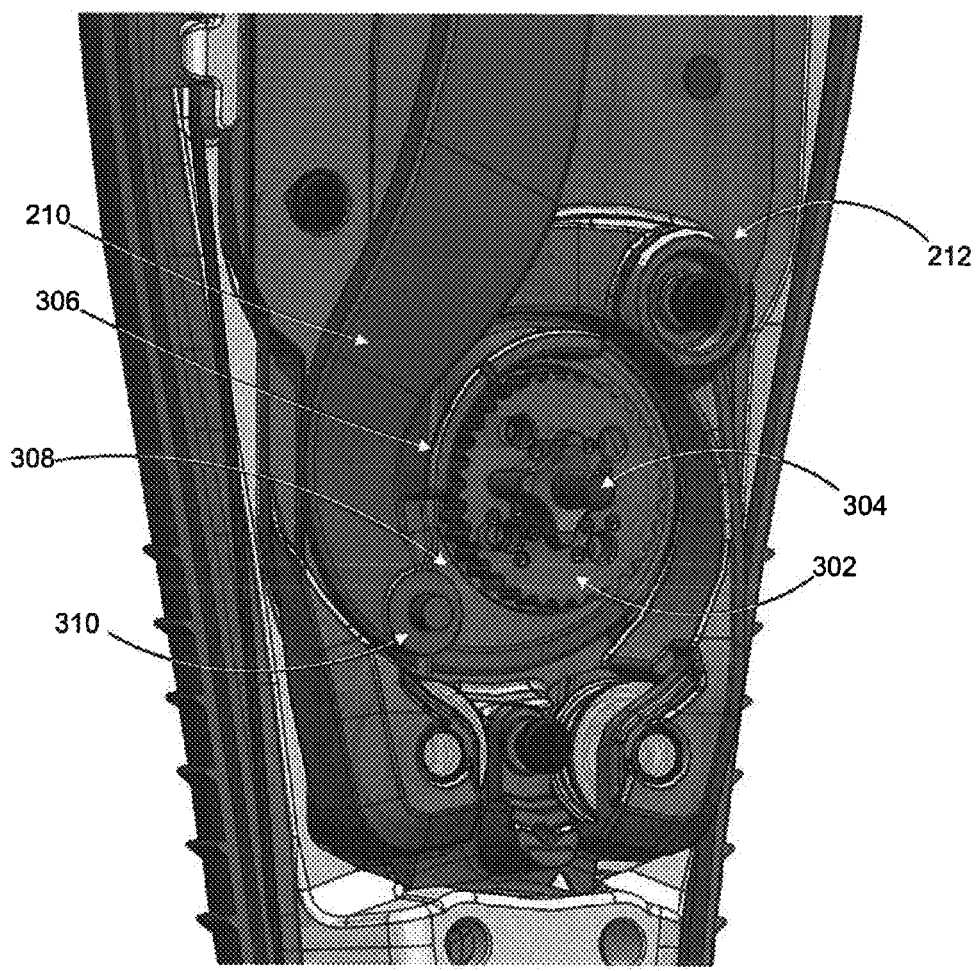

FIGS. 3A and 3B illustrate an example rocker assembly 212 within the surgical tool 100 of FIG. 1 in accordance with this disclosure. As shown here, the rocker assembly 212 includes a gear 302 that rotates around a central axle 304. The gear 302 engages the drive belt 204 so that rotation of the gear 302 creates rotation of the drive belt 204. A cap 306 helps to keep the drive belt 204 engaged against the gear 302.

The gear 302 is attached to a connecting link 308, which pivots around the central axle 304. The connecting link 308 is also attached to the gear 302 so that rotation of the connecting link 308 causes rotation of the gear 302. The linkage arm 210 is rotatably coupled to the connecting link 308 at a connection point 310.

When the linkage arm 210 is moved upward in FIG. 2, the linkage arm 210 pulls up on the connecting link 308, rotating the gear 302 in one direction (clockwise). When the linkage arm 210 is moved downward in FIG. 2, the linkage arm 210 pushes down on the connecting link 308, rotating the gear 302 in another direction (counterclockwise). Since the cap 306 helps keep the drive belt 204 engaged against the gear 302, the rotation of the gear 302 causes rotation of the drive belt 204, which also causes rotation of the surgical blade 202.

Note that in FIG. 1, the lower end of the surgical tool 100 could be angled with respect to the remainder of the tool 100. For example, the tip of the surgical tool 100 containing the surgical blade assembly 104 could be at an angle of about 10° (or other value). This can be done to facilitate easier viewing of the surgical blade assembly 104 by an operator during use of the tool 100. However, because of this angling, the drive belt 204 may be manipulated within the surgical tool 100 so that it can be properly driven by the components 206-214 (which may be operating in one plane) to turn the surgical blade 202 (which may be operating in another plane). In some embodiments, this can be handled as follows. In between the rocker assembly 212 and the surgical blade 202, the drive belt 204 can be rotated about 90°, and the angle of travel of the drive belt 204 can be adjusted by 10° (or other amount) to align the belt 204 with the surgical blade 202. The angle of travel can be adjusted in any suitable manner, such as by using pulleys or laying the belt 204 flat over a rounded ridge. However the belt's angle of travel is adjusted, the belt 204 can then be rotated back about 90° before reaching the surgical blade 202. Note than any other suitable technique can be used to alter the drive belt's angle with respect to the surgical blade 202.

Also note that the surgical tool 100 could include one or more mechanisms for helping to create a suitable amount of tension on the drive belt 204. In some embodiments, the entire drive mechanism shown in FIG. 2 could be movable, such as when the drive mechanism can slide up and down linearly and can be locked in place. In other embodiments, an idler pulley could be inserted in the drive mechanism, such as near the rocker assembly 212. The drive belt 204 could run over a portion of the idler pulley (such as over about 30°-45° of the pulley) between the surgical blade 202 and the rocker assembly 212. The position of the idler pulley could be adjustable, such as by using a screw/cam adjustment, so that the amount of tension on the belt 204 changes. Note than any other suitable technique can be used to alter the drive belt's tension.

Figure 4:
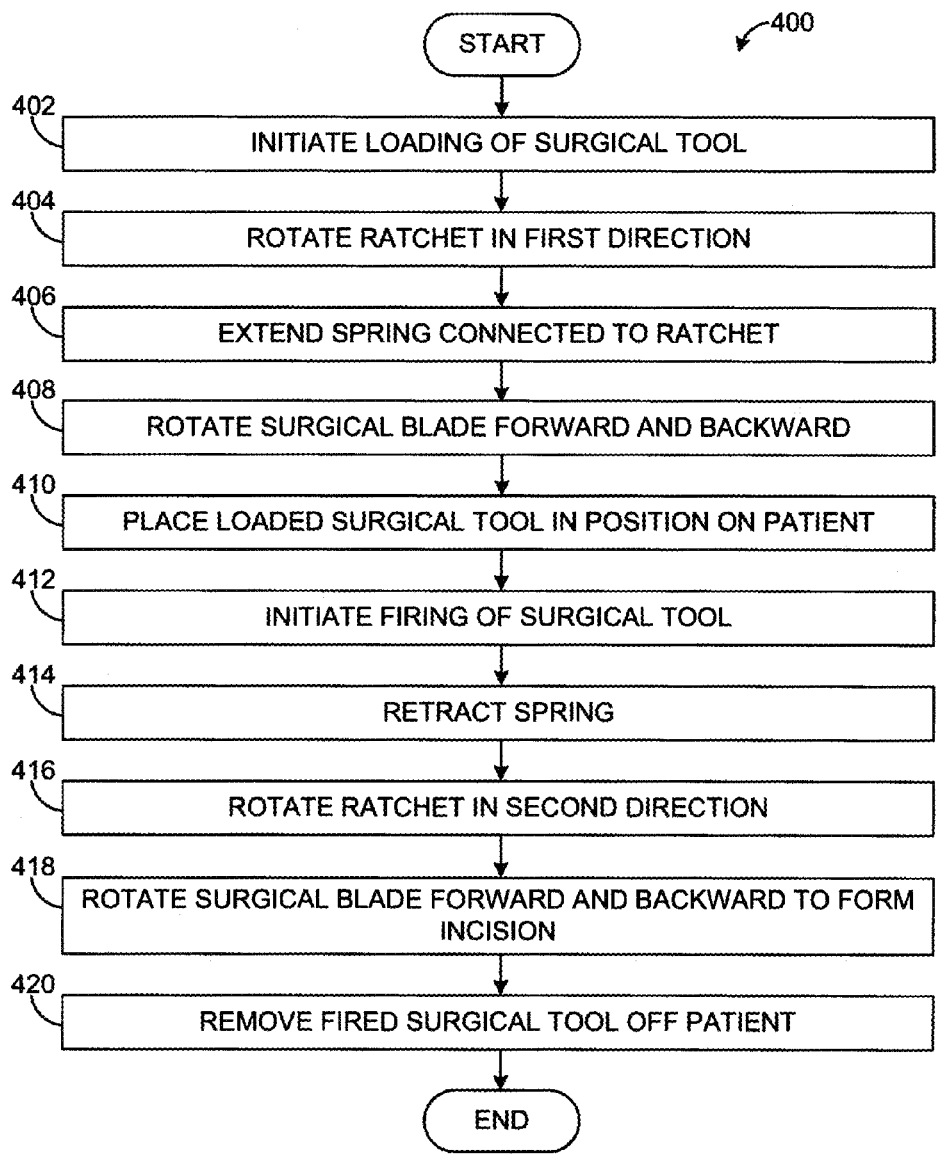
FIG. 4 illustrates an example method for making incisions in ocular tissue in accordance with this disclosure.

FIG. 4 illustrates an example method 400 for making incisions in ocular tissue in accordance with this disclosure. Various steps in FIG. 4 are also illustrated in FIGS. 5A through 5K. FIGS. 5A through 5K illustrate example operations of the surgical tool 100 of FIG. 1 in accordance with this disclosure.

Figure 5A:
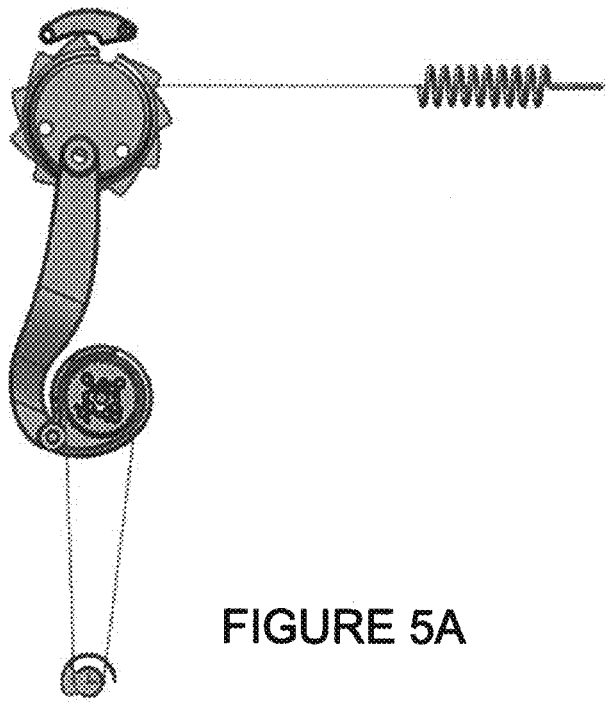
FIGS. 5A through 5K illustrate example operations of the surgical tool of FIG. 1 in accordance with this disclosure.

As shown in FIG. 4, loading of the surgical tool is initiated at step 402. Prior to loading, the surgical tool 100 may be at rest as shown in FIG. 5A. In this state, there may be little or no tension on the spring 214, and the surgical blade 202 is full retracted in what is referred to as the "home" position.

Figure 5B:
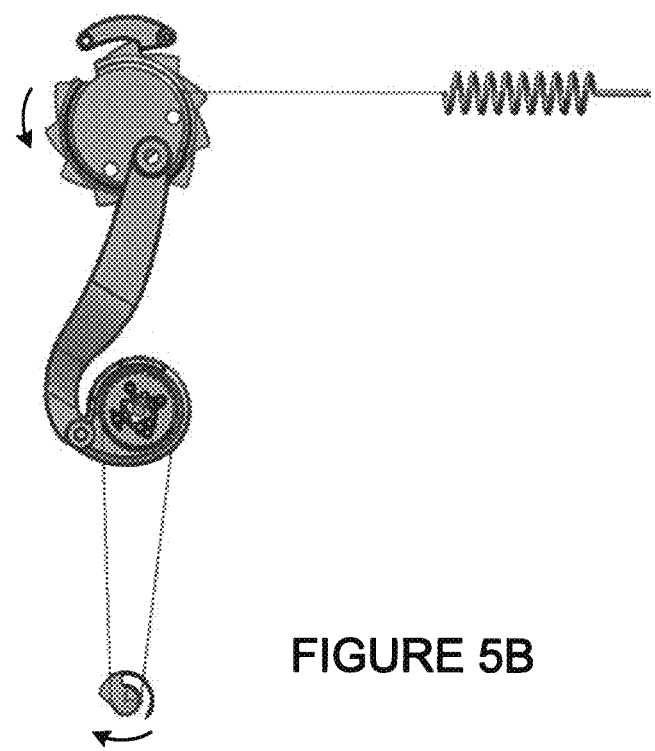
Figure 5C:
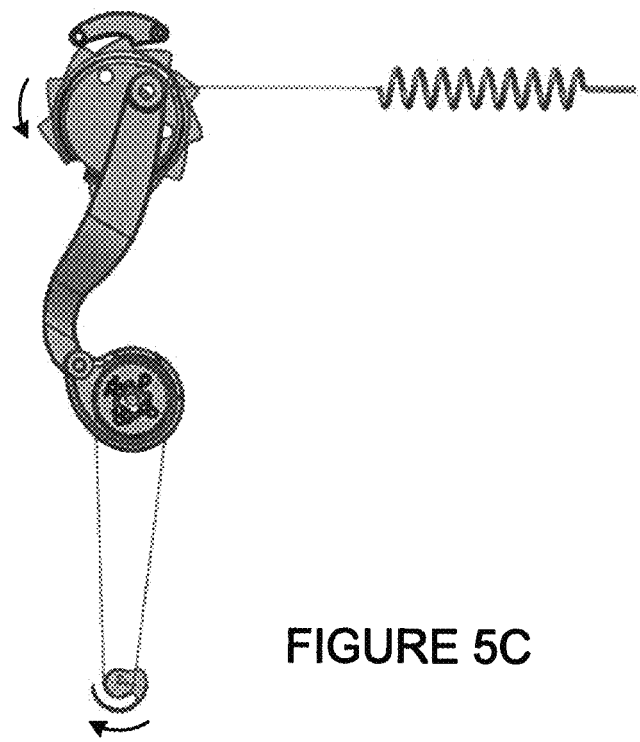
Figure 5D:
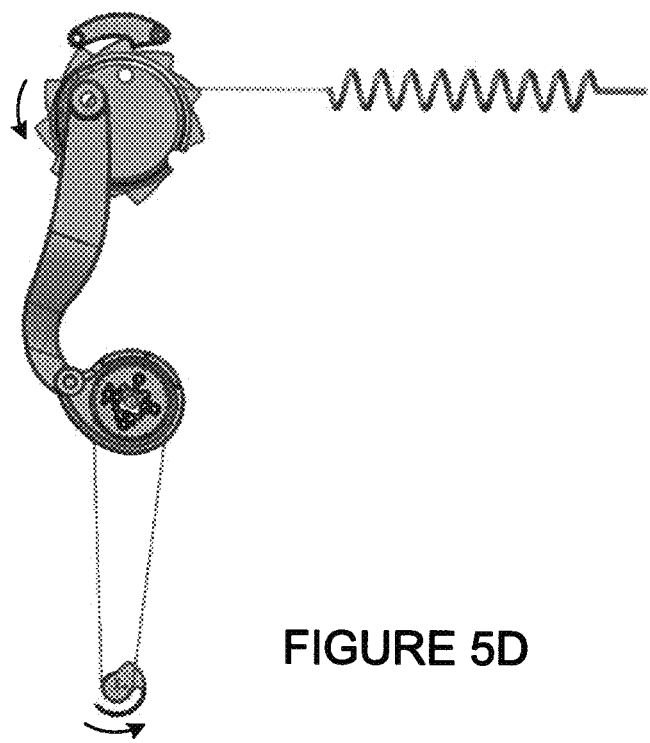
Figure 5E:
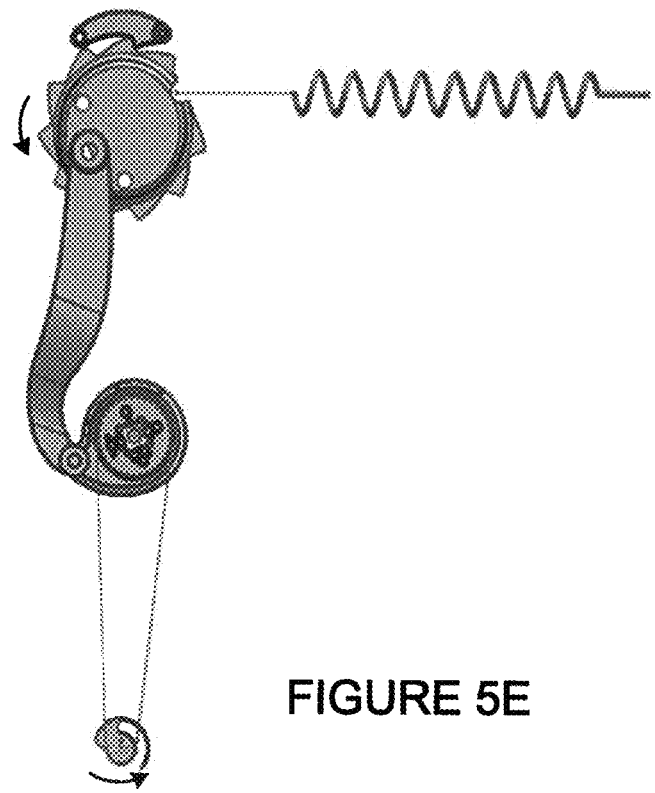

When loading is initiated, a ratchet in the surgical tool is rotated in a first direction at step 404. This extends the spring in the surgical tool at step 406 and rotates the surgical blade in the surgical tool forward and backward at step 408. The ratchet 206 could be turned, for example, using the knob 106. In some embodiments, the knob 106 is removable. This could allow the surgical tool 100 to be loaded using the knob 106, and the knob 106 could then be removed so that the knob 106 does not rotate when the tool 100 is later fired. In other embodiments, the knob 106 could be designed so that it rotates the ratchet 206 when pushed inward and then turned, and the knob 106 would remain stationary if it is not pushed inward (even if the ratchet 206 rotates). FIGS. 5B and 5C illustrate the first half of the rotation of the ratchet 206 in the first direction, causing the linkage arm 210 to move upward and the surgical blade 202 to rotate forward. FIGS. 5D and 5E illustrate the second half of the rotation of the ratchet 206 in the first direction, causing the linkage arm 210 to move downward and the surgical blade 202 to rotate backward. During this time, the pawl 208 helps to prevent the ratchet 206 from rotating in the wrong direction during loading. As seen here, a single rotation of the ratchet 206 causes the surgical blade 202 to rotate both forward and backward.

Figure 5F:
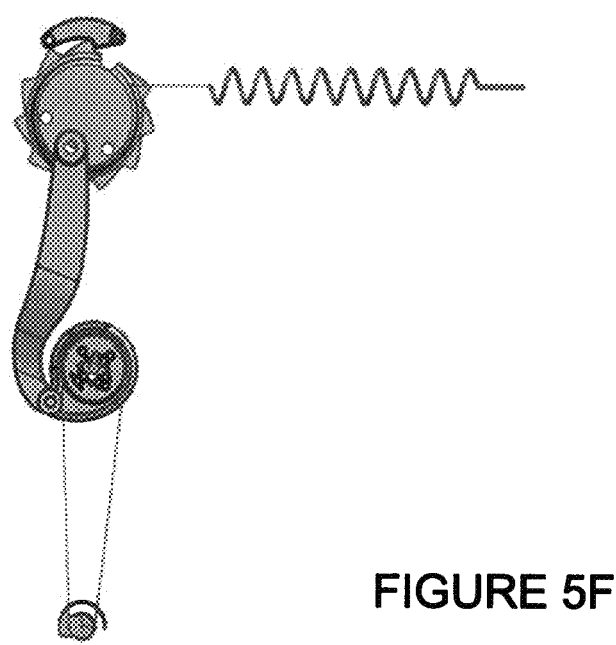

At this point, the surgical tool 100 has been loaded and is in the state shown in FIG. 5F, where there is significant tension on the spring 214 and the surgical blade 202 is in the "home" position. One benefit obtained using the loading process is that an operator can confirm whether the surgical blade 202 rotates forward and backward during the loading, helping to verify the proper operation of the surgical tool 100. The loaded surgical tool is placed on a patient at step 410. This could include, for example, placing the surgical tool 100 on the patient's eye.

Figure 5G:
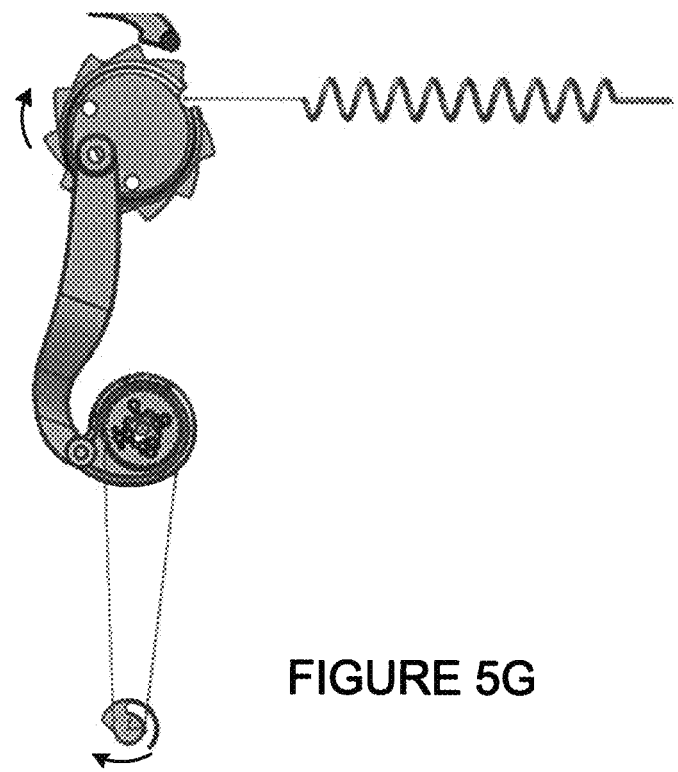
Figure 5H:
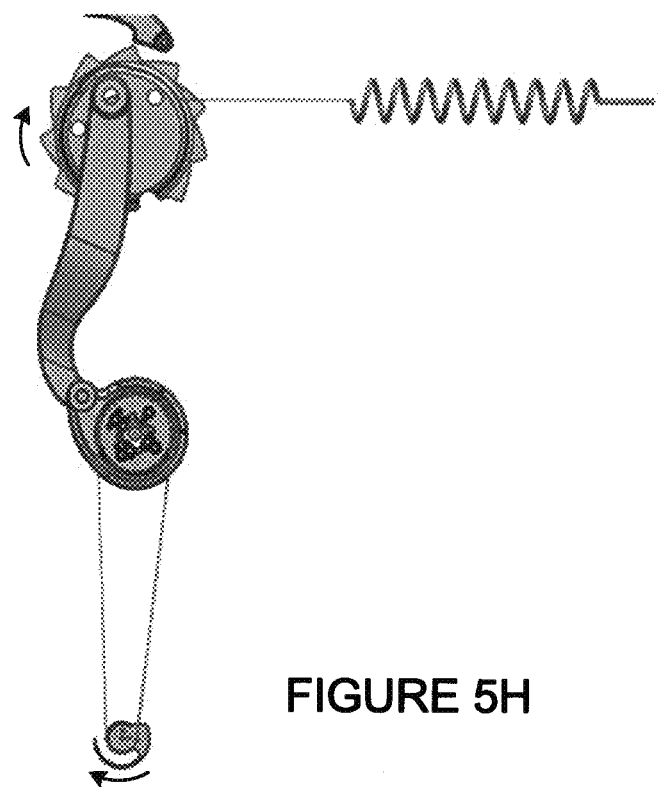
Figure 5I:
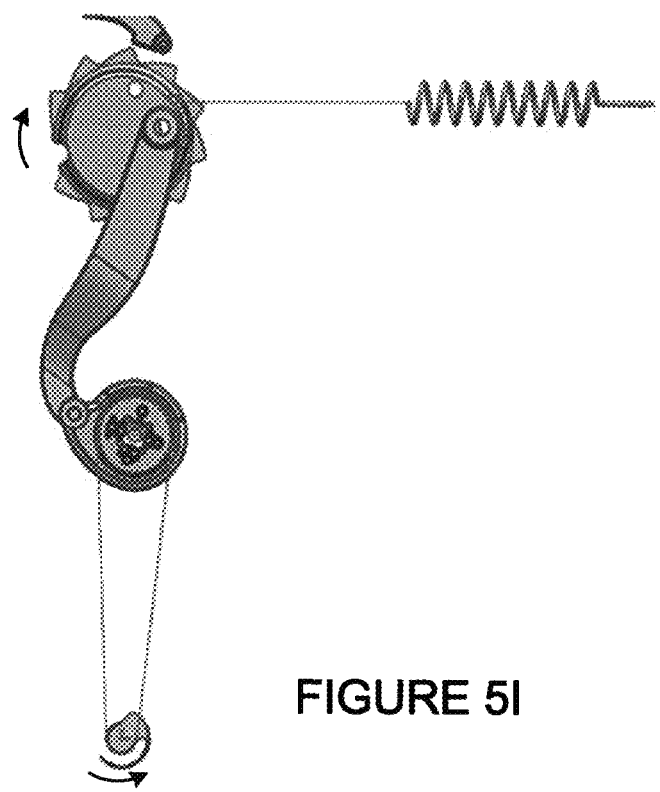
Figure 5J:
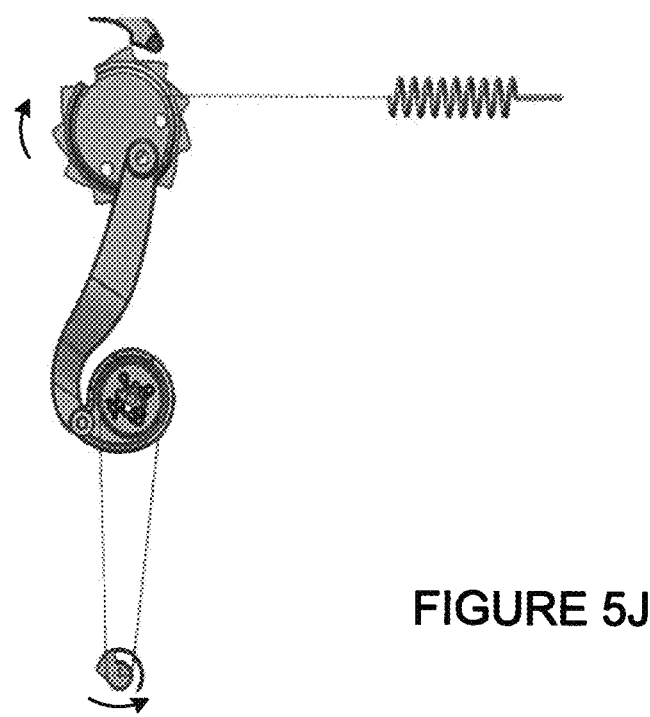
Figure 5K:
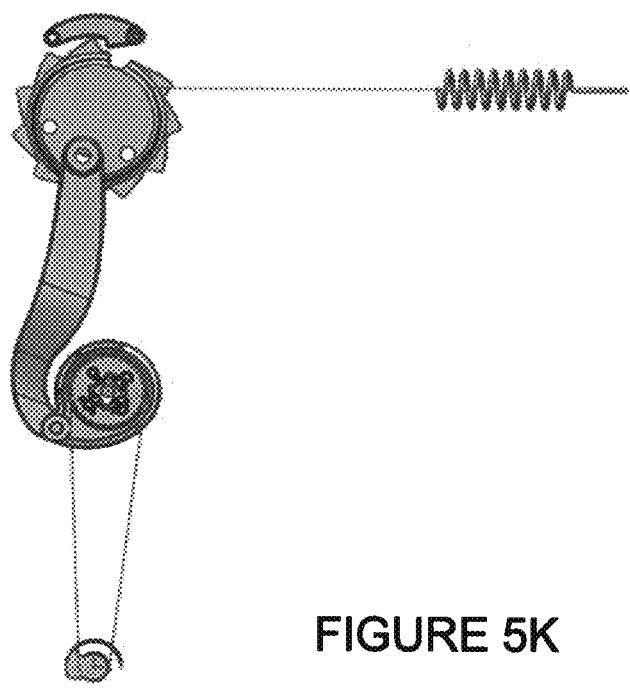

Firing of the surgical tool is initiated at step 412. This could include, for example, the operator triggering the surgical tool 100 using the trigger 108, causing the pawl 208 to release the ratchet 206. When firing is initiated, the spring retracts at step 414. This rotates the ratchet in a second direction at step 416 and rotates the surgical blade forward and backward again to form an incision at step 418. FIGS. 5G and 5H illustrate the first half of the rotation of the ratchet 206 in the second direction, causing the linkage arm 210 to move upward and the surgical blade 202 to rotate forward (into a patient's tissue). FIGS. 5I and 5J illustrate the second half of the rotation of the ratchet 206 in the second direction, causing the linkage arm 210 to move downward and the surgical blade 202 to rotate backward (out of the patient's tissue). This completes the formation of an incision. Once again, as seen here, a single rotation of the ratchet 206 causes the surgical blade 202 to rotate both forward and backward.

At this point, the surgical tool has been fired and is in the state shown in FIG. 5K, where again there is little or no tension on the spring 214 and the surgical blade 202 is in the "home" position. The fired surgical tool is removed from the patient at step 420. The surgical tool 100 could then be reused, such as by placing the surgical tool 100 in a different position on the patient and repeating steps 402-420.

Although FIG. 4 illustrates one example of a method 400 for making incisions in ocular tissue, various changes may be made to FIG. 4. For example, while shown as a series of steps, various steps in FIG. 4 could overlap, occur in parallel, occur in a different order, or occur multiple times. As specific examples, steps 404-408 could occur at the same time during loading, and steps 414-418 could occur at the same time during firing.

Although FIGS. 5A through 5K illustrate examples of operations of the surgical tool 100 of FIG. 1, various changes may be made to FIGS. 5A through 5K. For example, the method 400 could be used with other surgical tools and is not limited to the specific surgical tool 100 shown in FIG. 1.

In the surgical tool drive mechanism shown in FIG. 2, the rotation of the ratchet 206 in the clockwise direction (when the tool 100 is fired) can be limited so that the ratchet 206 cannot over-rotate. If over-rotation occurs, the ratchet 206 could cause the surgical blade 202 to begin rotating forward again, possibly back into the patient's tissue a second time. While a hard stop mechanism could be used, this could create considerable shock within the surgical tool 100. Even if such shock might not harm a patient, it could shorten the operational lifespan of the surgical tool 100 considerably.

Figure 6:
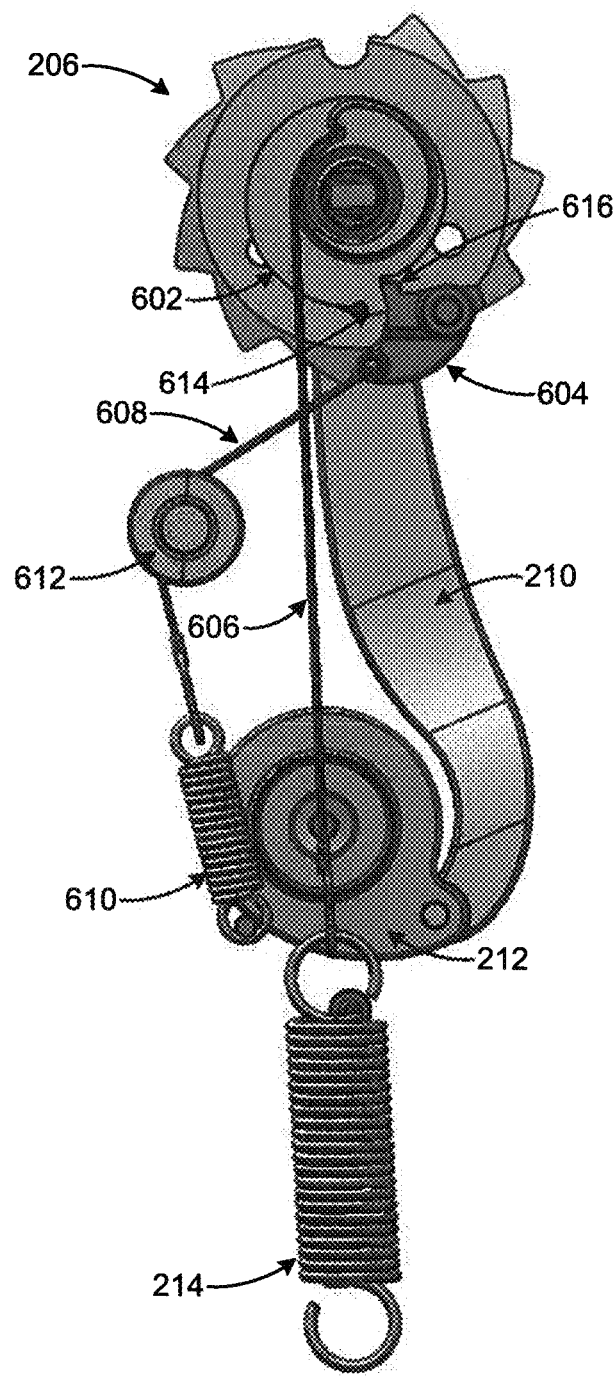
FIG. 6 illustrates an example mechanism for rotation stopping and shock absorption in the surgical tool of FIG. 1 in accordance with this disclosure.

FIG. 6 illustrates an example mechanism for rotation stopping and shock absorption in the surgical tool 100 of FIG. 1 in accordance with this disclosure. This mechanism could be used to stop rotation of the ratchet 206 after firing and prevent over-rotation or bounce-back of the ratchet 206. This mechanism also helps with shock absorption.

As shown in FIG. 6, the back sides of the ratchet 206, the linkage arm 210, and the rocker assembly 212 are shown (assuming the tool 100 is in the unloaded state). A take-up drum 602 is located on the back of the ratchet 206, and a take-up drum stop 604 is also attached to the ratchet 206. One end of the spring 214 is connected via a wire 606 to the ratchet 206, and the wire 606 is wrapped around the take-up drum 602. Also, the take-up drum stop 604 is connected via a wire 608 to another spring 610. The wire 608 is looped at least partially around a pulley 612. The spring 610 represents a pre-loaded spring.

As the ratchet 206 is rotated during loading (clockwise rotation in this view), a tab 614 from the take-up drum 602 turns with it. When the tool 100 is fully loaded, this tab 614 is resting just counter-clockwise from a tab 616 located on the take-up drum stop 604. When the tool 100 is fired, the take-up drum 602 rotates rapidly counterclockwise until the tab 614 on the take-up drum 602 strikes the tab 616 on the take-up drum stop 604. The take-up drum stop 604 is able to rotate somewhat but is constrained by the pre-loaded spring 610, thus absorbing much of the energy in the rotating ratchet 206. This can help to reduce or prevent damage to the assembly and assure a smooth end to the cutting cycle.

Although FIG. 6 illustrates one example of a mechanism for rotation stopping and shock absorption in the surgical tool of FIG. 1, various changes may be made in FIG. 6. For example, any other suitable technique could be used for stopping rotation and/or shock absorption. In embodiments where the surgical tool 100 is discarded after use, long-term operation of the tool 100 may not be required, and shock absorption may be unnecessary.

In the above description, various references are made to relative directions and orientations, such as left, right, clockwise, counterclockwise, and vertical. These relative directions and orientations are made with reference to the figures only and do not imply and specific structural limitations. Also provided are specific angles, such as 10° or 90°. These values are approximations only and are example values, so other values could be used.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "at least one of," when used with a list of items, means that different combinations of one or more of the listed items may be used, and only one item in the list may be needed. For example, "at least one of A, B, and C" includes any of the following combinations: A, B, C, A and B, A and C, B and C, and A and B and C. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
 rotating a ratchet in a first direction to extend a spring in a surgical tool;
 rotating a surgical blade forward and backward a first time based on the rotation of the ratchet in the first direction;

locking the ratchet after the rotation in the first direction to place the surgical tool in a loaded state;

firing the loaded surgical tool by releasing the ratchet so that the ratchet rotates in a second direction as the spring pulls the ratchet; and rotating the surgical blade forward and backward a second time based on the rotation of the ratchet in the second direction.

2. The method of claim 1, wherein rotating the surgical blade the first time comprises:

moving a linkage arm rotatably connected to the ratchet up and down as the ratchet is rotated in the first direction; and rotating a gear based on the movement of the linkage arm, the gear rotating a drive belt in order to rotate the surgical blade.

3. The method of claim 2, wherein:

the gear rotates around a central axle; and rotating the gear comprises pivoting a connecting link around the central axle, the connecting link attached to the gear, the linkage arm rotatably connected to the connecting link such that movement of the linkage arm causes the connecting link to pivot and rotate the gear.

4. The method of claim 2, further comprising:

holding the drive belt against the gear.

5. The method of claim 1, wherein:

locking the ratchet in place comprises locking the ratchet using a pawl; and firing the loaded surgical tool comprises pivoting the pawl.

6. The method of claim 5, wherein pivoting the pawl comprises operating a trigger to move the pawl.

7. The method of claim 1, wherein rotating the ratchet in the first direction comprises using a knob that is rotated by an operator.

8. A method comprising:

rotating a spring-loaded ratchet in a first direction to extend a spring;

rotating a gear a first time in response to rotating the spring-loaded ratchet in the first direction;

retracting the spring to rotate the spring-loaded ratchet in a second direction;

rotating the gear a second time in response to rotating the spring-loaded ratchet in the second direction; and rotating a surgical blade forward and backward when the gear is rotated the first time and forward and backward when the gear is rotated the second time.

9. The method of claim 8, wherein rotating the gear the first time comprises:

moving a linkage arm connected to the spring-loaded ratchet; and moving a connecting link that is connected to the linkage arm and the gear.

10. The method of claim 8, further comprising:

locking the spring-loaded ratchet in place using a pawl after rotating the spring-loaded ratchet in the first direction; and firing the surgical tool by pivoting the pawl to trigger the retracting of the spring.

11. The method of claim 10, wherein pivoting the pawl comprises operating a trigger to move the pawl.

12. The method of claim 8, further comprising:

holding a drive belt against the gear, the gear rotating the drive belt in order to rotate the surgical blade.

13. The method of claim 8, wherein rotating the spring-loaded ratchet in the first direction comprises using a knob that is rotated by an operator.

14. The method of claim 13, wherein the knob is removable.

15. A method comprising:

connecting a surgical blade to a driver, the surgical blade comprising a curved cutting blade and a central portion connected to the curved cutting blade, the central portion configured to be connected to the driver; and operating the driver to rotate the surgical blade, wherein operating the driver comprises:

rotating a ratchet in a first direction to extend a spring and rotate the surgical blade forward and backward a first time;

locking the ratchet after the rotation in the first direction;

releasing the ratchet so that the ratchet rotates in a second direction as the spring pulls the ratchet; and rotating the surgical blade forward and backward a second time based on the rotation of the ratchet in the second direction.

16. The method of claim 15, wherein rotating the ratchet in the first direction moves a linkage arm rotatably connected to the ratchet, the linkage arm rotating a gear that rotates the surgical blade.

17. The method of claim 16, wherein:

the gear rotates around a central axle; and a connecting link pivots around the central axle, the connecting link attached to the gear, the linkage arm rotatably connected to the connecting link such that movement of the linkage arm causes the connecting link to pivot and rotate the gear.

18. The method of claim 16, further comprising:

holding a drive belt against the gear, the drive belt imparting rotation to the surgical blade.

19. The method of claim 15, wherein:

locking the ratchet in place comprises locking the ratchet using a pawl; and releasing the ratchet comprises pivoting the pawl.

20. The method of claim 15, wherein rotating the ratchet in the first direction comprises using a knob that is rotated by an operator.

* * * * *